(12) United States Patent
Miki (10) Patent No.: US 11,370,728 B2
(45) Date of Patent: Jun. 28, 2022

(54) HYDROCARBON PRODUCTION METHOD AND PRODUCTION APPARATUS

(71) Applicant: ZEON CORPORATION, Tokyo (JP)

(72) Inventor: Hideaki Miki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 11 days.

(21) Appl. No.: 16/487,100

(22) PCT Filed: Feb. 21, 2018

(86) PCT No.: PCT/JP2018/006271
§ 371 (c)(1),
(2) Date: Aug. 20, 2019

(87) PCT Pub. No.: WO2018/163828
PCT Pub. Date: Sep. 13, 2018

(65) Prior Publication Data
US 2019/0375697 A1 Dec. 12, 2019

(30) Foreign Application Priority Data
Mar. 8, 2017 (JP) .............................. JP2017-044288

(51) Int. Cl.
*C07C 5/333* (2006.01)
*C07C 2/52* (2006.01)
(Continued)

(52) U.S. Cl.
CPC .............. *C07C 5/333* (2013.01); *B01D 3/143* (2013.01); *B01D 3/40* (2013.01); *B01J 19/245* (2013.01);
(Continued)

(58) Field of Classification Search
None
See application file for complete search history.

(56) References Cited

U.S. PATENT DOCUMENTS 2,354,895 A * 8/1944 Ward .............................. 585/362
2,421,506 A * 6/1947 Jones ............................. 585/256
(Continued)

FOREIGN PATENT DOCUMENTS

CN 103459565 A 12/2013
JP 2005350475 A 12/2005
(Continued)

OTHER PUBLICATIONS

LibreTexts "Le Chatelier's Principle Fundamentals" pp. 1-5, 2021 (Year: 2021).*

(Continued)

*Primary Examiner* — In Suk C Bullock
*Assistant Examiner* — Alyssa L Cepluch
(74) *Attorney, Agent, or Firm* — Kenja IP Law PC (57) ABSTRACT

A hydrocarbon production method for producing hydrocarbons from a hydrocarbon mixture includes: a first extractive distillation step of performing extractive distillation of an extractive distillation target to obtain a fraction (A) in which isoprene and piperylene are enriched and a fraction (B) in which a linear hydrocarbon and a branched hydrocarbon are enriched; a first distillation step of obtaining a fraction (C) in which isoprene is enriched and a fraction (D) in which piperylene is enriched from the fraction (A); a dehydrogenation step of performing dehydrogenation or oxidative dehydrogenation of either or both of the linear hydrocarbon and the branched hydrocarbon contained in the fraction (B) to obtain a dehydrogenated product; and a recovery step of supplying the dehydrogenated product to an extractive distillation column or a distillation column and obtaining isoprene and/or piperylene from the dehydrogenated product.

3 Claims, 2 Drawing Sheets

(51) Int. Cl.
*C07C 5/48* (2006.01)
*C07C 7/08* (2006.01)
*B01D 3/14* (2006.01)
*B01D 3/40* (2006.01)
*B01J 19/24* (2006.01)
*C07C 5/03* (2006.01)
*C07C 7/00* (2006.01)
*C07C 7/04* (2006.01)

(52) U.S. Cl.
CPC .................. *C07C 2/52* (2013.01); *C07C 5/03* (2013.01); *C07C 5/48* (2013.01); *C07C 7/005* (2013.01); *C07C 7/04* (2013.01); *C07C 7/08* (2013.01); *C07C 2603/68* (2017.05)

(56) References Cited

U.S. PATENT DOCUMENTS 2,458,082 A * 1/1949 Kilpatrick ..................... 585/627
3,077,744 A * 2/1963 Craig ....................... C07C 11/18
　　　　　　　　　　　　　　　　　　　　62/618
3,557,239 A * 1/1971 Gebhart, Jr. ............ C07C 7/005
　　　　　　　　　　　　　　　　　　　　585/362
3,557,240 A * 1/1971 Gebhart, Jr. ............. C07C 7/177
　　　　　　　　　　　　　　　　　　　　585/362
2014/0024867 A1　1/2014　Yachi et al.

FOREIGN PATENT DOCUMENTS

| | | |
|---|---|---|
| JP | 2014208603 A | 11/2014 |
| JP | 2015151391 A | 8/2015 |
| WO | 2012133732 A1 | 10/2012 |

OTHER PUBLICATIONS

Sep. 10, 2019, International Preliminary Report on Patentability issued in the International Patent Application No. PCT/JP2018/006271.

\* cited by examiner

HYDROCARBON PRODUCTION METHOD AND PRODUCTION APPARATUS

TECHNICAL FIELD

The present disclosure relates to a hydrocarbon production method and production apparatus and, in particular, relates to a hydrocarbon production method using extractive distillation and a hydrocarbon production apparatus using extractive distillation.

BACKGROUND

Methods using extractive distillation are known as methods for separation and recovery of unsaturated hydrocarbons such as isoprene that are useful as monomers from a mixture of hydrocarbons having a carbon number of 5, such as a C5 fraction obtained in the manufacture of ethylene through cracking of naphtha.

In a process of separating and recovering a hydrocarbon such as isoprene from a C5 fraction by extractive distillation, attempts are being made to increase the efficiency with which a feedstock is used through effective use of residues (raffinates).

In one specific example, Patent Literature (PTL) 1 proposes a technique of hydrogenating an extraction residue oil (raffinate) obtained after isoprene is separated from a C5 fraction by extractive distillation, and then returning the resultant hydrogenated product to an ethylene center for use as a gasoline base material or a feedstock for an ethylene cracker.

In another example, PTL 2 proposes a technique for producing isoprene in a high yield through dehydrogenation of isoamylene in an extraction residue oil (raffinate) obtained after isoprene is separated from a C5 fraction by extractive distillation.

CITATION LIST

Patent Literature

PTL 1: WO 2012/133732 A1
PTL 2: JP 2014-208603 A

SUMMARY

Technical Problem

A C5 fraction also contains unsaturated hydrocarbons other than isoprene, such as piperylene (1,3-pentadiene), that are also useful as monomers. However, the conventional techniques described above focus only on efficiently producing isoprene and do not enable efficient production of both isoprene and piperylene.

Accordingly, an objective of the present disclosure is to provide a hydrocarbon production method and production apparatus with which isoprene and piperylene can be efficiently obtained from a hydrocarbon mixture containing hydrocarbons having a carbon number of 5, such as a C5 fraction.

Solution to Problem

Specifically, the present disclosure aims to advantageously solve the problem set forth above by disclosing a hydrocarbon production method for producing hydrocarbons from a hydrocarbon mixture containing isoprene, piperylene, a linear hydrocarbon having a carbon number of 5 and including one or fewer carbon-carbon double bonds, and a branched hydrocarbon having a carbon number of 5 and including one or fewer carbon-carbon double bonds, comprising: a first extractive distillation step of using a first extractive distillation column to perform extractive distillation of an extractive distillation target including the hydrocarbon mixture or a pretreated hydrocarbon mixture resulting from pretreatment of the hydrocarbon mixture to obtain a fraction (A) in which isoprene and piperylene are enriched and a fraction (B) in which the linear hydrocarbon and the branched hydrocarbon, having lower solubility than isoprene and piperylene in an extractant used in the extractive distillation, are enriched; a first distillation step of using a first distillation column to perform distillation of a fraction obtained after separation of the extractant from the fraction (A) to obtain a fraction (C) in which isoprene is enriched and a fraction (D) in which piperylene is enriched; a dehydrogenation step of performing dehydrogenation or oxidative dehydrogenation of either or both of the linear hydrocarbon and the branched hydrocarbon contained in the fraction (B) to obtain a dehydrogenated product including either or both of a linear hydrocarbon dehydrogenated product containing piperylene and a branched hydrocarbon dehydrogenated product containing isoprene; and a recovery step of supplying the dehydrogenated product to an extractive distillation column or a distillation column and obtaining either or both of isoprene and piperylene from the dehydrogenated product.

By performing the first extractive distillation step and the first distillation step to obtain the fraction (C) in which isoprene is enriched and the fraction (D) in which piperylene is enriched, and by also performing dehydrogenation or oxidative dehydrogenation in the dehydrogenation step of the fraction (B) discharged in the first extractive distillation step and then obtaining isoprene and/or piperylene from the resultant dehydrogenated product as set forth above, the efficiency with which the hydrocarbon mixture serving as a feedstock is used can be increased, and isoprene and piperylene can be efficiently obtained.

In the presently disclosed hydrocarbon production method, the dehydrogenated product is preferably supplied to the first extractive distillation column in the recovery step. This is because isoprene and piperylene can be obtained more efficiently without providing an additional extractive distillation column or distillation column when the dehydrogenated product is supplied to the first extractive distillation column for use as part of the extractive distillation target.

In the presently disclosed hydrocarbon production method, the dehydrogenation step preferably includes: a step of separating the linear hydrocarbon and the branched hydrocarbon contained in the fraction (B); and a step of performing dehydrogenation or oxidative dehydrogenation of either or both of the linear hydrocarbon and the branched hydrocarbon that have been separated. By separating the linear hydrocarbon and the branched hydrocarbon and then performing dehydrogenation or oxidative dehydrogenation, the linear hydrocarbon and the branched hydrocarbon can each be dehydrogenated or oxidatively dehydrogenated under conditions that are appropriate for the corresponding hydrocarbon. Moreover, this enables separate adjustment of the production amounts of the linear hydrocarbon dehydrogenated product and the branched hydrocarbon dehydrogenated product.

The presently disclosed hydrocarbon production method preferably further comprises a step of determining a required production amount of isoprene and piperylene, wherein an amount of either or both of the linear hydrocarbon and the branched hydrocarbon that is dehydrogenated or oxidatively dehydrogenated in the dehydrogenation step is adjusted in accordance with the required production amount that is determined. This is because the desired amount of isoprene and piperylene can be efficiently obtained by adjusting the amount of either or both of the linear hydrocarbon and the branched hydrocarbon that is dehydrogenated or oxidatively dehydrogenated in accordance with the required production amount of isoprene and piperylene.

In the presently disclosed hydrocarbon production method, it is preferable that the hydrocarbon mixture further contains cyclopentadiene, the extractive distillation target includes the pretreated hydrocarbon mixture, and the pretreatment includes: a step of dimerizing cyclopentadiene in the hydrocarbon mixture to obtain a hydrocarbon mixture containing dicyclopentadiene; and a step of using a predistillation column to perform distillation of the hydrocarbon mixture containing dicyclopentadiene to obtain the pretreated hydrocarbon mixture and a fraction (E) in which dicyclopentadiene is enriched. This is because dicyclopentadiene, which is useful as a monomer, can be efficiently obtained in addition to isoprene and piperylene by dimerizing cyclopentadiene and then obtaining the fraction (E) in which dicyclopentadiene is enriched in the predistillation column. Moreover, by obtaining the fraction (E) in which dicyclopentadiene is enriched in the predistillation column, the concentration of piperylene in the fraction (D) obtained in the first distillation step can be sufficiently increased.

The presently disclosed hydrocarbon production method preferably further comprises: an isoprene purification step of purifying the fraction (C) in an isoprene purification section including a second extractive distillation column to obtain high-purity isoprene; a piperylene purification step of purifying the fraction (D) in a piperylene purification section to obtain high-purity piperylene; a dicyclopentadiene purification step of purifying the fraction (E) in a dicyclopentadiene purification section to obtain high-purity dicyclopentadiene; and a hydrogenation step of hydrogenating at least one of a residue discharged in the isoprene purification step, a residue discharged in the piperylene purification step, and a residue discharged in the dicyclopentadiene purification step. Through hydrogenation of a residue in the hydrogenation step, a hydrogenated product is obtained that can favorably be used as a gasoline base material or a feedstock for an ethylene cracker.

In the presently disclosed hydrocarbon production method, it is preferable that either or both of the linear hydrocarbon and the branched hydrocarbon are dehydrogenated in the dehydrogenation step, and residue hydrogenation in the hydrogenation step is performed using hydrogen produced in dehydrogenation of either or both of the linear hydrocarbon and the branched hydrocarbon in the dehydrogenation step. This is because the efficiency with which the hydrocarbon mixture serving as a feedstock is used can be further increased and hydrocarbons can be produced even more efficiently when hydrogen that is produced in dehydrogenation of either or both of the linear hydrocarbon and the branched hydrocarbon is used in the hydrogenation step.

Moreover, the present disclosure aims to advantageously solve the problem set forth above by disclosing a hydrocarbon production apparatus for producing hydrocarbons from a hydrocarbon mixture containing isoprene, piperylene, a linear hydrocarbon having a carbon number of 5 and including one or fewer carbon-carbon double bonds, and a branched hydrocarbon having a carbon number of 5 and including one or fewer carbon-carbon double bonds, comprising: a first extractive distillation column that performs extractive distillation of an extractive distillation target including the hydrocarbon mixture or a pretreated hydrocarbon mixture resulting from pretreatment of the hydrocarbon mixture; a stripping column that separates an extractant from a fraction (A) that flows out from the bottom of the first extractive distillation column; a first distillation column that performs distillation of a fraction obtained by separating the extractant from the fraction (A) in the stripping column; a dehydrogenation section that performs dehydrogenation or oxidative dehydrogenation of at least a portion of a fraction (B) that flows out from the top of the first extractive distillation column to obtain a dehydrogenated product; and a dehydrogenated product line that supplies the dehydrogenated product obtained in the dehydrogenation section to an extractive distillation column or a distillation column.

Through inclusion of the first extractive distillation column, the stripping column, and the first distillation column as set forth above, a fraction in which isoprene is enriched and a fraction in which piperylene is enriched can be obtained from the hydrocarbon mixture. Moreover, through inclusion of the dehydrogenation section and the dehydrogenated product line, either or both of the linear hydrocarbon and the branched hydrocarbon contained in the fraction (B) can be dehydrogenated or oxidatively dehydrogenated, either or both of a linear hydrocarbon dehydrogenated product containing piperylene and a branched hydrocarbon dehydrogenated product containing isoprene can be obtained, and piperylene and/or isoprene can be recovered. Consequently, the efficiency with which the hydrocarbon mixture serving as a feedstock is used can be increased, and isoprene and piperylene can be efficiently obtained.

In the presently disclosed hydrocarbon production apparatus, the dehydrogenated product line preferably supplies the dehydrogenated product to the first extractive distillation column. This is because isoprene and piperylene can be obtained more efficiently without providing an additional extractive distillation column or distillation column when the dehydrogenated product is supplied to the first extractive distillation column.

In the presently disclosed hydrocarbon production apparatus, the dehydrogenation section preferably includes a separator that is capable of separating the linear hydrocarbon and the branched hydrocarbon, and a dehydrogenator that performs dehydrogenation or oxidative dehydrogenation of either or both of the linear hydrocarbon and the branched hydrocarbon that are separated in the separator. By providing the separator and by performing dehydrogenation after separating the linear hydrocarbon and the branched hydrocarbon, the linear hydrocarbon and the branched hydrocarbon can each be dehydrogenated under conditions that are appropriate for the corresponding hydrocarbon in the dehydrogenator. Moreover, this enables separate adjustment of the production amounts of the linear hydrocarbon dehydrogenated product and the branched hydrocarbon dehydrogenated product.

In the presently disclosed hydrocarbon production apparatus, it is preferable that the hydrocarbon mixture further contains cyclopentadiene, and the hydrocarbon production apparatus further comprises, upstream of the first extractive distillation column as viewed in a direction of flow of the hydrocarbon mixture: a dimerizer that dimerizes cyclopentadiene in the hydrocarbon mixture to obtain a hydrocarbon mixture containing dicyclopentadiene; and a predistillation column that performs distillation of the hydrocarbon mixture containing dicyclopentadiene to obtain the pretreated hydrocarbon mixture. This is because dicyclopentadiene, which is useful as a monomer, can be efficiently obtained in addition to isoprene and piperylene through inclusion of the dimerizer and the predistillation column upstream of the first extractive distillation column. Moreover, this makes it possible to obtain a fraction containing high-concentration piperylene in the first distillation column.

The presently disclosed hydrocarbon production apparatus preferably further comprises: an isoprene purification section that includes a second extractive distillation column and that purifies a fraction (C) that flows out from the top of the first distillation column to obtain high-purity isoprene; a piperylene purification section that purifies a fraction (D) that flows out from the bottom of the first distillation column to obtain high-purity piperylene; a dicyclopentadiene purification section that purifies a fraction (E) that flows out from the bottom of the predistillation column to obtain high-purity dicyclopentadiene; and a hydrogenator that performs hydrogenation of at least one of a residue discharged from the isoprene purification section, a residue discharged from the piperylene purification section, and a residue discharged from the dicyclopentadiene purification section. This is because a hydrogenated product that can favorably be used as a gasoline base material or a feedstock for an ethylene cracker can be obtained when the hydrogenator is included and hydrogenation of a residue is performed.

In the presently disclosed hydrocarbon production apparatus, it is preferable that either or both of the linear hydrocarbon and the branched hydrocarbon are dehydrogenated in the dehydrogenator, and the hydrocarbon production apparatus further comprises a hydrogen line that supplies the hydrogenator with hydrogen produced in the dehydrogenator. This is because the efficiency with which the hydrocarbon mixture serving as a feedstock is used can be further increased and hydrocarbons can be produced even more efficiently when hydrogen that is produced in the dehydrogenator is used to perform hydrogenation.

Advantageous Effect

According to the present disclosure, it is possible to efficiently obtain isoprene and piperylene from a hydrocarbon mixture containing hydrocarbons having a carbon number of 5, such as a C5 fraction.

DETAILED DESCRIPTION

The following provides a detailed description of embodiments of the present disclosure.

The presently disclosed hydrocarbon production method can be used to obtain useful hydrocarbons such as isoprene and piperylene from a mixture of hydrocarbons having a carbon number of 5, such as a C5 fraction. Moreover, the presently disclosed hydrocarbon production apparatus can suitably be used to obtain useful hydrocarbons such as isoprene and piperylene using the presently disclosed hydrocarbon production method, for example.

(Hydrocarbon Production Method)

The presently disclosed hydrocarbon production method is a method of producing hydrocarbons from a hydrocarbon mixture containing isoprene, piperylene, a linear hydrocarbon having a carbon number of 5 and including one or fewer carbon-carbon double bonds, and a branched hydrocarbon having a carbon number of 5 and including one or fewer carbon-carbon double bonds.

The presently disclosed hydrocarbon production method includes a first extractive distillation step of using a first extractive distillation column to perform extractive distillation of an extractive distillation target including the hydrocarbon mixture or a pretreated hydrocarbon mixture after the hydrocarbon mixture serving as a feedstock has optionally been subjected to pretreatment. The presently disclosed hydrocarbon production method also includes a first distillation step of using a first distillation column to perform distillation of a fraction that is obtained after separating an extractant used in the extractive distillation from a fraction (A) that is obtained in the first extractive distillation step and in which isoprene and piperylene are enriched. The presently disclosed hydrocarbon production method also includes a dehydrogenation step of performing dehydrogenation or oxidative dehydrogenation of either or both of the linear hydrocarbon having a carbon number of 5 and including one or fewer carbon-carbon double bonds (hereinafter, also referred to simply as the "linear hydrocarbon") and the branched hydrocarbon having a carbon number of 5 and including one or fewer carbon-carbon double bonds (hereinafter, also referred to simply as the "branched hydrocarbon") contained in a fraction (B) that is obtained in the first extractive distillation step and in which the linear hydrocarbon and the branched hydrocarbon are enriched. The presently disclosed hydrocarbon production method also includes a recovery step of supplying a dehydrogenated product that is obtained in the dehydrogenation step to an extractive distillation column or a distillation column, and obtaining isoprene and/or piperylene from the dehydrogenated product. The presently disclosed hydrocarbon production method may optionally further include a hydrogenation step of performing hydrogenation of a residue that is discharged in the process of obtaining hydrocarbons such as isoprene and piperylene from the hydrocarbon mixture.

In the presently disclosed hydrocarbon production method, the steps set forth above are preferably implemented repeatedly so as to continuously produce hydrocarbons.

The following describes the hydrocarbon mixture serving as a feedstock and each of the steps in order.

<Hydrocarbon Mixture>

The hydrocarbon mixture serving as a feedstock contains isoprene, piperylene, a linear hydrocarbon having a carbon number of 5 and including one or fewer carbon-carbon double bonds, and a branched hydrocarbon having a carbon number of 5 and including one or fewer carbon-carbon double bonds, and may optionally further contain other hydrocarbons such as cyclopentadiene and dicyclopentadiene. The hydrocarbon mixture may, for example, be a hydrocarbon mixture containing hydrocarbons having a carbon number of 5 as a main component, such as a C5 fraction obtained in the manufacture of ethylene through cracking of naphtha, but is not specifically limited thereto.

The phrase "containing hydrocarbons having a carbon number of 5 as a main component" as used in the present disclosure means that the total content of hydrocarbons having a carbon number of 5 in the hydrocarbon mixture is 50 mol % or more.

The linear hydrocarbon having a carbon number of 5 and including one or fewer carbon-carbon double bonds may, for example, be one or more hydrocarbons selected from the group consisting of n-pentane, 1-pentene, and 2-pentene.

Moreover, the branched hydrocarbon having a carbon number of 5 and including one or fewer carbon-carbon double bonds may, for example, be one or more hydrocarbons selected from the group consisting of isopentane, 2-methyl-1-butene, 3-methyl-1-butene, and 2-methyl-2-butene.

<Pretreatment>

In a case in which the hydrocarbon mixture serving as a feedstock contains cyclopentadiene, the hydrocarbon mixture may be subjected to pretreatment in the presently disclosed hydrocarbon production method. Specifically, pretreatment that includes a step of dimerizing cyclopentadiene in the hydrocarbon mixture to obtain a hydrocarbon mixture containing dicyclopentadiene and a step of using a predistillation column to perform distillation of the hydrocarbon mixture containing dicyclopentadiene to obtain a pretreated hydrocarbon mixture and a fraction (E) in which dicyclopentadiene is enriched may be implemented before the first extractive distillation step is implemented in the presently disclosed hydrocarbon production method.

Dicyclopentadiene, which is a hydrocarbon that is useful as a monomer or the like, can be efficiently obtained from the hydrocarbon mixture by implementing this pretreatment. Moreover, by implementing this pretreatment, inclusion of cyclopentadiene and dicyclopentadiene in a fraction obtained in the subsequently described first distillation step can be prevented. As a consequence, a fraction having a sufficiently high piperylene concentration can be obtained in the first distillation step.

The dimerization of cyclopentadiene may be carried out be any reaction format without any specific limitations so long as a dimerization reaction proceeds. From a viewpoint of inhibiting oligomerization of cyclopentadiene and a viewpoint of reaction efficiency, the dimerization of cyclopentadiene is preferably carried out by a Diels-Alder reaction, and more preferably by a Diels-Alder reaction in a liquid phase using a catalyst-free continuous reactor.

In a case in which a Diels-Alder reaction is implemented using a continuous reactor, the residence time of the hydrocarbon mixture is preferably 0.5 hours or more, and more preferably 1 hour or more, and is preferably 6 hours or less, and more preferably 4 hours or less. A residence time that is too short may result in insufficient progress of the dimerization reaction. Moreover, a residence time that is too long may lower the purity of obtained dicyclopentadiene due to the occurrence of side reactions of cyclopentadiene with isoprene, piperylene, and the like.

The reaction temperature in dimerization of cyclopentadiene is preferably 50° C. or higher, and more preferably 60° C. or higher, and is preferably 250° C. or lower, and more preferably 150° C. or lower. This is because it is difficult for the dimerization reaction to proceed if the reaction temperature is too low. On the other hand, an oligomerization reaction may proceed if the reaction temperature is too high.

The distillation of the hydrocarbon mixture containing dicyclopentadiene in a predistillation column may be carried out using any distillation column and distillation conditions without any specific limitations so long as a fraction (E) in which dicyclopentadiene is enriched and a pretreated hydrocarbon mixture can be obtained.

Note that the fraction (E) in which dicyclopentadiene is enriched normally flows out from the bottom of the predistillation column, whereas the pretreated hydrocarbon mixture normally flows out from the top of the predistillation column. The pretreated hydrocarbon mixture normally contains isoprene, piperylene, a linear hydrocarbon having a carbon number of 5 and including one or fewer carbon-carbon double bonds, and a branched hydrocarbon having a carbon number of 5 and including one or fewer carbon-carbon double bonds.

A dicyclopentadiene purification step of purifying the fraction (E) obtained in the pretreatment in a dicyclopentadiene purification section may be implemented in the presently disclosed hydrocarbon production method to obtain dicyclopentadiene of even higher purity. By raising the purity of dicyclopentadiene to higher than in the fraction (E) through implementation of this dicyclopentadiene purification step, the obtained dicyclopentadiene can be used particularly favorably as a monomer or the like.

Purification of dicyclopentadiene in the dicyclopentadiene purification section may be carried out using any distillation column and distillation conditions without any specific limitations. High-purity dicyclopentadiene normally flows out from the top of the distillation column, whereas a residue normally flows out from the bottom of the distillation column.

<First Extractive Distillation Step>

In the first extractive distillation step, extractive distillation of an extractive distillation target including the hydrocarbon mixture or the pretreated hydrocarbon mixture is performed in a first extractive distillation column. A fraction (A) in which isoprene and piperylene are enriched is obtained from the bottom of the first extractive distillation column, whereas a fraction (B) in which the linear hydrocarbon and the branched hydrocarbon, having lower solubility than isoprene and piperylene in an extractant used in the extractive distillation, are enriched is obtained from the top of the first extractive distillation column. The extractant used in the extractive distillation normally becomes contained in the fraction (A).

No specific limitations are placed on the extractant used in the extractive distillation other than being an extractant that can dissolve and extract conjugated dienes having a carbon number of 5 such as isoprene and piperylene. For example, the extractant may be an extractant that is described in JP 2005-350475 A. Of such extractants, dimethylformamide is preferable. Moreover, various additives such as described in JP 2005-350475 A may be added to the extractant.

<First Distillation Step>

In the first distillation step, a fraction obtained after the extractant is separated from the fraction (A) that flows out from the bottom of the first extractive distillation column in the first extractive distillation step is distilled in a first distillation column to obtain a fraction (C) in which isoprene is enriched and a fraction (D) in which piperylene is enriched.

Separation of the extractant from the fraction (A) is not specifically limited and may, for example, be carried out using a stripping column. Extractant that has been separated from the fraction (A) and flows out from the bottom of the stripping column may be reused in extractive distillation.

The distillation in the first distillation column of the fraction obtained after separation of the extractant from the fraction (A) may be carried out using any distillation column and distillation conditions without any specific limitations so long as a fraction (C) in which isoprene is enriched and a fraction (D) in which piperylene is enriched can be obtained.

The fraction (D) in which piperylene is enriched normally flows out from the bottom of the first distillation column, whereas the fraction (C) in which isoprene is enriched normally flows out from the top of the first distillation column. In a case in which the previously described pretreatment is implemented in the presently disclosed hydrocarbon production method, inclusion of cyclopentadiene and the like in the fraction (D) can be prevented, and a fraction (D) having high piperylene concentration can be obtained.

An isoprene purification step of purifying the fraction (C) obtained in the first distillation step in an isoprene purification section may be implemented in the presently disclosed hydrocarbon production method to obtain high-purity isoprene having even higher purity. By raising the purity of isoprene to higher than in the fraction (C) through implementation of the isoprene purification step, the obtained isoprene can be used particularly favorably as a monomer or the like.

The purification of isoprene in the isoprene purification section is not specifically limited and may be carried out using a second extractive distillation column. Specifically, the purification of isoprene can be carried out using an isoprene purification section that, for example, includes a second extractive distillation column that performs extractive distillation of the fraction (C) and a second distillation column that performs distillation of a fraction that flows out from the top of the second extractive distillation column, and optionally further includes a stripping column that separates an extractant from a fraction that flows out from the bottom of the second extractive distillation column and a purification column that purifies a fraction that flows out from the top of the second distillation column.

The extractant used in the second extractive distillation column may be the same as any of the extractants that can be used in the first extractive distillation column. A fraction in which isoprene is enriched relative to the fraction (C) flows out from the top of the second extractive distillation column, whereas a fraction containing the extractant flows out from the bottom of the second extractive distillation column. The fraction that flows out from the bottom of the second extractive distillation column can be separated into a residue and the extractant in the stripping column. Extractant that flows out from the bottom of the stripping column may be reused in extractive distillation.

In the second distillation column, the fraction that flows out from the top of the second extractive distillation column can be distilled to obtain high-purity isoprene. A fraction containing acetylenes such as 2-butyne normally flows out from the top of the second distillation column, whereas a fraction containing high-purity isoprene normally flows out from the bottom of the second distillation column.

The fraction that flows out from the top of the second distillation column may optionally be purified in the purification column in the isoprene purification step to obtain high-purity 2-butyne.

Moreover, a piperylene purification step of purifying the fraction (D) obtained in the first distillation step in a piperylene purification section may be implemented in the presently disclosed hydrocarbon production method to obtain high-purity piperylene having even higher purity. By raising the purity of piperylene to higher than in the fraction (D) through implementation of the piperylene purification step, the obtained piperylene can be used particularly favorably as a monomer or the like.

Purification of piperylene in the piperylene purification section may be carried out using any distillation column and distillation conditions without any specific limitations. High-purity piperylene normally flows out from the top of the distillation column, whereas a residue normally flows out from the bottom of the distillation column.

<Dehydrogenation Step>

In the dehydrogenation step, either or both of the linear hydrocarbon and the branched hydrocarbon contained in the fraction (B) that flows out from the top of the first extractive distillation column in the first extractive distillation step are dehydrogenated or oxidatively dehydrogenated to obtain a dehydrogenated product including either or both of a linear hydrocarbon dehydrogenated product containing piperylene and a branched hydrocarbon dehydrogenated product containing isoprene.

The term "dehydrogenation" as used in the present disclosure refers to a reaction in which hydrogen is eliminated as a hydrogen molecule ($H_2$) (simple dehydrogenation), whereas the term "oxidative dehydrogenation" as used in the present disclosure refers to a reaction in which hydrogen is eliminated as a water molecule in the presence of oxygen. It is preferable that either or both of the linear hydrocarbon and the branched hydrocarbon are dehydrogenated in the dehydrogenation step from a viewpoint that the produced hydrogen can be used, for example, in a hydrogenation step that is described in detail further below.

In the dehydrogenation step, all of the linear hydrocarbon and the branched hydrocarbon contained in the fraction (B) may be dehydrogenated or oxidatively dehydrogenated, or, alternatively, only a portion thereof may be dehydrogenated or oxidatively dehydrogenated. Moreover, just one of the linear hydrocarbon and the branched hydrocarbon contained in the fraction (B) may be dehydrogenated or oxidatively dehydrogenated in the dehydrogenation step, or, alternatively, both of the linear hydrocarbon and the branched hydrocarbon may be dehydrogenated or oxidatively dehydrogenated in the dehydrogenation step.

Piperylene and/or isoprene are recovered from the dehydrogenated product obtained in the dehydrogenation step as described in detail further below (i.e., the dehydrogenated product becomes a feedstock of isoprene and piperylene in addition to the hydrocarbon mixture or pretreated hydrocarbon mixture). Therefore, the amount of the linear hydrocarbon and/or branched hydrocarbon that is dehydrogenated or oxidatively dehydrogenated in the dehydrogenation step is preferably the amount that is required for production of isoprene and/or piperylene.

In other words, it is preferable that a step of determining a required production amount of isoprene and piperylene is implemented in the presently disclosed hydrocarbon production method and that the amount of the linear hydrocarbon and/or branched hydrocarbon that is dehydrogenated or oxidatively dehydrogenated in the dehydrogenation step is adjusted in accordance with the required production amount that is determined. More specifically, dehydrogenation or oxidative dehydrogenation of the linear hydrocarbon and/or the branched hydrocarbon in the dehydrogenation step is preferably performed in a manner such that a difference (shortfall) between the required production amount and the amount of isoprene or piperylene that can be produced from the hydrocarbon mixture or the pretreated hydrocarbon mixture is supplemented by isoprene and/or piperylene produced in the dehydrogenation step.

Note that linear hydrocarbon and/or branched hydrocarbon that is not dehydrogenated or oxidatively dehydrogenated in the dehydrogenation step may, for example, be mixed with a hydrogenated product obtained in the subsequently described hydrogenation step and used as a gasoline base material or a feedstock for an ethylene cracker, but is not specifically limited to being used in this manner.

In the dehydrogenation step, it is preferable that the linear hydrocarbon and the branched hydrocarbon contained in the fraction (B) are separated prior to dehydrogenation or oxidative dehydrogenation. In other words, the dehydrogenation step preferably includes a step of separating the linear hydrocarbon and the branched hydrocarbon contained in the fraction (B) and a step of performing dehydrogenation or oxidative dehydrogenation of either or both of the linear hydrocarbon and the branched hydrocarbon that have been separated. By separating the linear hydrocarbon and the branched hydrocarbon in advance, the linear hydrocarbon and the branched hydrocarbon can each be dehydrogenated or oxidatively dehydrogenated under conditions that are appropriate for the corresponding hydrocarbon. Moreover, this enables separate adjustment of the production amounts of the linear hydrocarbon dehydrogenated product and the branched hydrocarbon dehydrogenated product.

Separation of the linear hydrocarbon and the branched hydrocarbon contained in the fraction (B) is not specifically limited and may be carried out by any separation method such as distillation, extractive distillation, distillation and separation via olefin to alcohol conversion, or membrane separation.

Of these methods, membrane separation is preferable as the separation method from viewpoints of productivity, apparatus scale, and energy consumption.

The separation membrane used in membrane separation may be a polymeric membrane, an inorganic membrane, a carbon membrane, or the like without any specific limitations other than being a membrane that can separate the linear hydrocarbon and the branched hydrocarbon.

Of these membranes, an inorganic membrane is preferable, a ceramic membrane, metal membrane, or alloy membrane is more preferable, a ceramic membrane is even more preferable, and a zeolite membrane such as a silicalite membrane is particularly preferable from viewpoints of heat resistance and chemical resistance.

Membrane separation of the linear hydrocarbon and the branched hydrocarbon can be carried out using any form of membrane separation module, such as a module of a flat plate, tube, laminate flat plate, or multitube type. Of these modules, a flat plate or multitube type membrane separation module is preferable from viewpoints of separation efficiency and small apparatus size, and a multitube type membrane separation module is more preferable from a viewpoint of ease of separation membrane replacement.

The dehydrogenation or oxidative dehydrogenation of the linear hydrocarbon and the branched hydrocarbon in the dehydrogenation step may be carried in a gas or liquid phase and in the presence or absence of a catalyst. However, from a viewpoint of production efficiency of a dehydrogenated product, it is preferable that the dehydrogenation or oxidative dehydrogenation is carried out in the presence of a catalyst, and more preferable that the dehydrogenation or oxidative dehydrogenation is carried out in a gas phase and in the presence of a solid catalyst.

Examples of reactors that may be used in the dehydrogenation or oxidative dehydrogenation include, but are not specifically limited to, a batch reactor, a complete mixing continuous reactor, a fixed bed continuous reactor, and a fluidized bed continuous reactor. Of these reactors, a fixed bed continuous reactor or a fluidized bed continuous reactor is preferable as the reactor used in dehydrogenation or oxidative dehydrogenation from a viewpoint of simplicity of operation.

Examples of catalysts that can be used in dehydrogenation include, but are not specifically limited to, metal catalysts, Cr-based oxide catalysts, Zr-based oxide catalysts, Fe-based oxide catalysts, and the like. Moreover, examples of catalysts that can be used in oxidative dehydrogenation include, but are not specifically limited to, complex oxide catalysts having Mo and Bi as main components.

A linear hydrocarbon dehydrogenated product containing piperylene can be generated through dehydrogenation or oxidative dehydrogenation of the linear hydrocarbon in the dehydrogenation step. Moreover, a branched hydrocarbon dehydrogenated product containing isoprene can be generated through dehydrogenation or oxidative dehydrogenation of the branched hydrocarbon in the dehydrogenation step.

Note that in addition to piperylene, the linear hydrocarbon dehydrogenated product may contain 1-pentene, 2-pentene, and 1,4-pentadiene produced through dehydrogenation or oxidative dehydrogenation of the linear hydrocarbon and may contain unreacted linear hydrocarbon. Moreover, in addition to isoprene, the branched hydrocarbon dehydrogenated product may contain 2-methyl-1-butene, 3-methyl-1-butene, and 2-methyl-2-butene produced through dehydrogenation or oxidative dehydrogenation of the branched hydrocarbon and may contain unreacted branched hydrocarbon.

Furthermore, hydrogen is produced in a case in which dehydrogenation of the linear hydrocarbon and/or branched hydrocarbon is performed in the dehydrogenation step. The produced hydrogen can be recovered without any specific limitations by pressure swing adsorption (PSA), solvent absorption, membrane separation, cryogenic separation, or the like. Of these methods, recovery of hydrogen by PSA or membrane separation is preferable, and recovery of hydrogen by membrane separation is more preferable.

Examples of separation membranes that may be used in membrane separation of hydrogen include, but are not specifically limited to, ceramic membranes, ceramic-metal composite membranes, carbon membranes, alloy membranes, and polymeric membranes. Of these membranes, ceramic membranes, ceramic-metal composite membranes, carbon membranes, and alloy membranes are preferable, and ceramic-metal composite membranes and alloy membranes are more preferable from viewpoints of heat resistance and mechanical strength.

Note that it is not necessary to implement dehydrogenation and hydrogen recovery separately in the dehydrogenation step. For example, dehydrogenation and hydrogen recovery may be performed concurrently using a membrane reactor or the like. Examples of hydrogen separation membranes that may be used in the membrane reactor include, but are not specifically limited to, carbon membranes, polymeric membranes, ceramic membranes (for example, zeolite membranes such as a silicalite membrane), metal-modified ceramic membranes (for example, metal-modified zeolite membranes), and alloy membranes. Of these membranes, carbon membranes, ceramic membranes (for example, zeolite membranes such as a silicalite membrane), metal-modified ceramic membranes (for example, metal-modified zeolite membranes), and alloy membranes are preferable as the hydrogen separation membrane, and metal-modified ceramic membranes (for example, metal-modified zeolite membranes) and alloy membranes are more preferable as the hydrogen separation membrane from viewpoints of heat resistance and dimensional stability.

<Recovery Step>

In the presently disclosed hydrocarbon production method, the dehydrogenated product obtained in the dehydrogenation step is supplied to an extractive distillation column or a distillation column, and piperylene and/or isoprene is recovered from the dehydrogenated product. Through this recovery, hydrocarbons contained in the fraction (B) can be effectively utilized, and isoprene and piperylene can be efficiently obtained from the hydrocarbon mixture.

In the recovery step, it is preferable that the dehydrogenated product is supplied to the first extractive distillation column and is used as part of the extractive distillation target. In other words, it is preferable that the first extractive distillation step and the first distillation step are implemented with respect to an extractive distillation target that includes the hydrocarbon mixture or the pretreated hydrocarbon mixture and also includes the dehydrogenated product in order that isoprene and piperylene are obtained from either or both of the linear hydrocarbon dehydrogenated product and the branched hydrocarbon dehydrogenated product in addition to being obtained from the hydrocarbon mixture or the pretreated hydrocarbon mixture. In continuous hydrocarbon production, by supplying the dehydrogenated product to the first extractive distillation column and then recovering isoprene and/or piperylene in the dehydrogenated product in conjunction with isoprene and piperylene in the hydrocarbon mixture or pretreated hydrocarbon mixture, isoprene and/or piperylene can be efficiently recovered without providing an additional extractive distillation column or distillation column for the dehydrogenated product.

Note that in a case in which pretreatment of the hydrocarbon mixture is performed in the presently disclosed hydrocarbon production method, it is preferable that the dehydrogenated product that is obtained in the dehydrogenation step is supplied to the first extractive distillation column after being mixed with the pretreated hydrocarbon mixture or is supplied directly to the first extractive distillation column. This is because the load on the predistillation column used in pretreatment increases if the dehydrogenated product is mixed with the hydrocarbon mixture prior to pretreatment.

Moreover, by supplying the first distillation column with the linear hydrocarbon dehydrogenated product containing piperylene that is obtained as the dehydrogenated product in the dehydrogenation step in the presently disclosed hydrocarbon production method, piperylene contained in the dehydrogenated product can be efficiently recovered in conjunction with piperylene contained in the fraction (A) without providing an additional extractive distillation column or distillation column for the dehydrogenated product.

Furthermore, by supplying the second extractive distillation column with the branched hydrocarbon dehydrogenated product containing isoprene that is obtained as the dehydrogenated product in the dehydrogenation step in the presently disclosed hydrocarbon production method, isoprene in the dehydrogenated product can be efficiently recovered in conjunction with isoprene contained in the fraction (C) without providing an additional extractive distillation column or distillation column for the dehydrogenated product.

However, it is preferable that the dehydrogenated product is supplied to the first extractive distillation column from a viewpoint that hydrocarbons other than piperylene that are contained in the linear hydrocarbon dehydrogenated product and hydrocarbons other than isoprene that are contained in the branched hydrocarbon dehydrogenated product can be used as the fraction (B) and from a viewpoint of obtaining high-purity piperylene and isoprene.

<Hydrogenation Step>

At least one and preferably all of a residue discharged in the isoprene purification step, a residue discharged in the piperylene purification step, and a residue discharged in the dicyclopentadiene purification step, which are described further above, are hydrogenated in the hydrogenation step.

The residue discharged in the isoprene purification step may, for example, be a fraction that flows out from the top of the stripping column when the extractant is separated from the fraction that flows out from the bottom of the second extractive distillation column; a fraction that flows out from the top of the second distillation column; or a fraction that flows out from the top of the purification column when high-purity 2-butyne is obtained through purification in the purification column of the fraction that flows out from the top of the second distillation column. The residue discharged in the piperylene purification step may, for example, be a fraction that flows out from the bottom of the distillation column in the piperylene purification section. The residue discharged in the dicyclopentadiene purification step may, for example, be a fraction that flows out from the bottom of the distillation column in the dicyclopentadiene purification section.

The hydrogenation may be carried in a gas or liquid phase and in the presence or absence of a catalyst. However, from a viewpoint of hydrogenation efficiency, it is preferable that the hydrogenation is carried out in the presence of a catalyst, and more preferable that the hydrogenation is carried out in a gas phase and in the presence of a solid catalyst.

Examples of reactors that may be used in the hydrogenation include, but are not specifically limited to, a batch reactor, a complete mixing continuous reactor, a fixed bed continuous reactor, and a fluidized bed continuous reactor. Of these reactors, a fixed bed continuous reactor or a fluidized bed continuous reactor is preferable as the reactor used in hydrogenation, and a fixed bed continuous reactor is more preferable as the reactor used in hydrogenation from a viewpoint of simplicity of operation.

Moreover, the hydrogenation is preferably carried out after thermal decomposition of the residue. This is because, in a situation in which the obtained hydrogenated product is used as a feedstock for an ethylene cracker, for example, the yield of ethylene or the like may decrease and staining of a cooler of the cracker may be exacerbated if the hydrogenation has been performed without thermal decomposition.

Examples of catalysts that can be used in the hydrogenation include, but are not specifically limited to, precious metal-based catalysts, Cu-based catalysts, Ni-based catalysts, and Zr-based catalysts. Of these catalysts, precious metal-based catalysts and Ni-based catalysts are preferable, and Ni-based catalysts are more preferable. This is because, in a situation in which the obtained hydrogenated product is used as a feedstock for an ethylene cracker, for example, the yield of ethylene or the like may decrease and staining of a cooler of the cracker may be exacerbated if hydrogenation is insufficient.

Examples of hydrogen that can be used in the hydrogenation include, but are not specifically limited to, reformer hydrogen in petroleum refining, electrolytic hydrogen, and hydrogen produced as a by-product from a fluid catalytic process. However, from viewpoints of further increasing the efficiency with which the hydrocarbon mixture serving as a feedstock is used and more efficiently producing hydrocarbons, it is preferable to use hydrogen that is produced in dehydrogenation of either or both of the linear hydrocarbon and the branched hydrocarbon in the dehydrogenation step.

The hydrogenated product obtained in the hydrogenation step can favorably be used, for example, as a gasoline base material or a feedstock for an ethylene cracker.

(Hydrocarbon Production Apparatus)

The presently disclosed hydrocarbon production apparatus is an apparatus for producing hydrocarbons from a hydrocarbon mixture containing isoprene, piperylene, a linear hydrocarbon having a carbon number of 5 and including one or fewer carbon-carbon double bonds, and a branched hydrocarbon having a carbon number of 5 and including one or fewer carbon-carbon double bonds.

Note that the hydrocarbon mixture may be the same as that used in the presently disclosed hydrocarbon production method set forth above. In the following, descriptions of configurations that are the same as those that can be used in the presently disclosed hydrocarbon production method set forth above are omitted.

Figure 1:
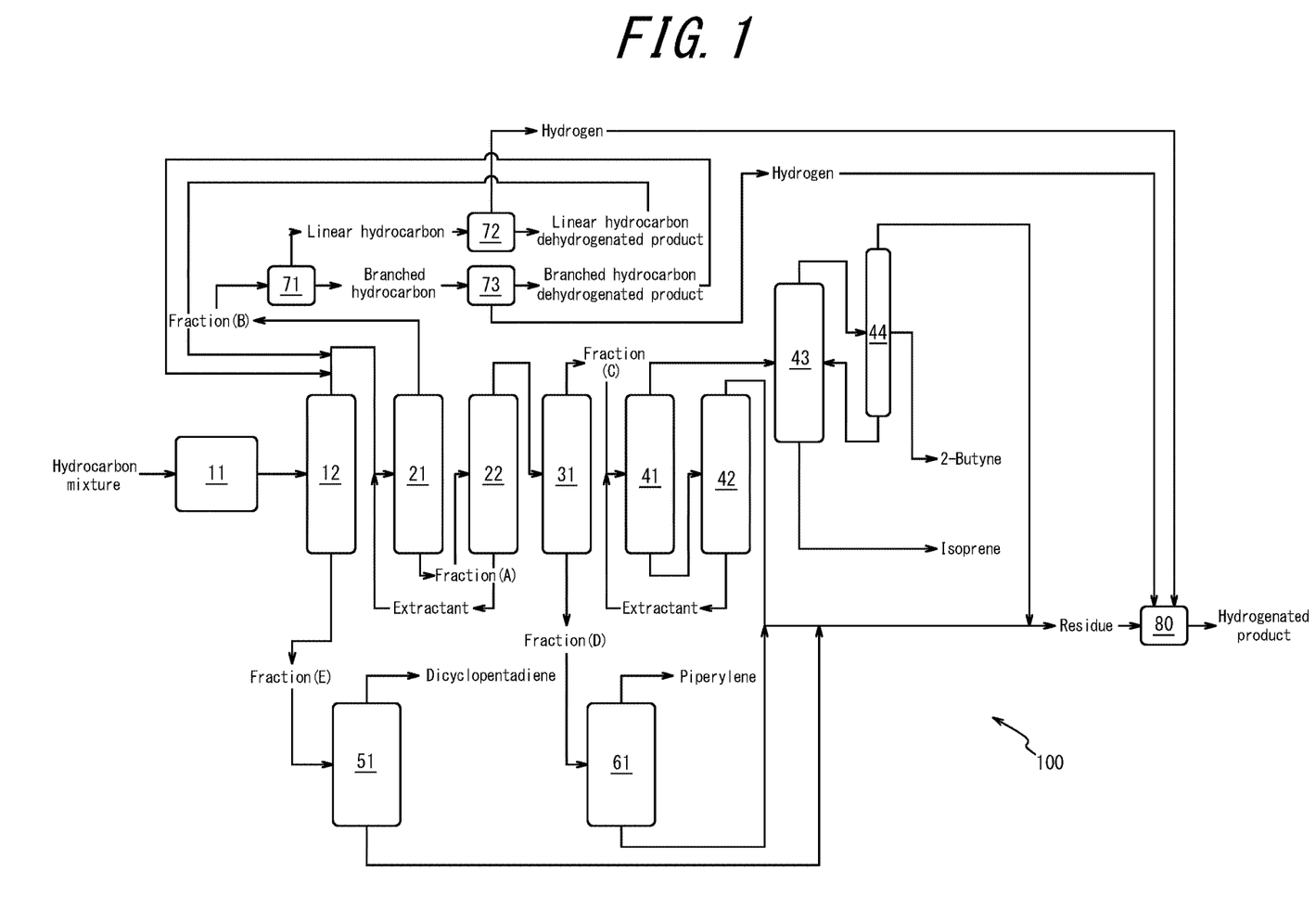
FIG. 1 is an explanatory diagram illustrating schematic configuration of one example of a hydrocarbon production apparatus conforming with the present disclosure.

One example of the presently disclosed hydrocarbon production apparatus may, for example, have a configuration such as illustrated in FIG. 1.

Specifically, a hydrocarbon production apparatus 100 illustrated in FIG. 1 includes a dimerizer 11 that performs dimerization of cyclopentadiene in the hydrocarbon mixture to obtain a hydrocarbon mixture containing dicyclopentadiene and a predistillation column 12 that performs distillation of the hydrocarbon mixture containing dicyclopentadiene to obtain a pretreated hydrocarbon mixture. The production apparatus 100 also includes a first extractive distillation column 21 that performs extractive distillation of an extractive distillation target including the pretreated hydrocarbon mixture that flows out from the predistillation column 12, a stripping column 22 that separates an extractant from a fraction (A) that flows out from the bottom of the first extractive distillation column 21, and a first distillation column 31 that performs distillation of a fraction obtained through separation of the extractant from the fraction (A) in the stripping column 22. Note that the extractant that is separated and recovered from the fraction (A) in the stripping column 22 may be returned to the first extractive distillation column 21 and reused in extractive distillation.

The production apparatus 100 also includes an isoprene purification section that purifies a fraction (C) that flows out from the top of the first distillation column 31 to obtain high-purity isoprene. Specifically, as this isoprene purification section, the production apparatus 100 includes a second extractive distillation column 41 into which the fraction (C) flows, a stripping column 42 that separates a fraction that flows out from the bottom of the second extractive distillation column 41 into a residue and extractant, a second distillation column 43 that performs distillation of a fraction that flows out from the top of the second extractive distillation column 41, and a purification column 44 that purifies a fraction that flows out from the top of the second distillation column 43. Note that the extractant that is separated and recovered in the stripping column 42 may be returned to the second extractive distillation column 41 and reused in extractive distillation.

The production apparatus 100 also includes a distillation column 61 as a piperylene purification section that purifies a fraction (D) that flows out from the bottom of the first distillation column 31 to obtain high-purity piperylene.

In addition, the production apparatus 100 includes a distillation column 51 as a dicyclopentadiene purification section that purifies a fraction (E) that flows out from the bottom of the predistillation column 12 to obtain high-purity dicyclopentadiene.

The production apparatus 100 further includes a dehydrogenation section that performs dehydrogenation or oxidative dehydrogenation (dehydrogenation in the illustrated example) of at least a portion of a fraction (B) (all of the fraction (B) in the illustrated example) that flows out from the top of the first extractive distillation column 21.

Specifically, as this dehydrogenation section, the production apparatus 100 includes a separator 71 into which the fraction (B) that flows out from the top of the first extractive distillation column 21 flows and that separates a linear hydrocarbon and a branched hydrocarbon contained in the fraction (B), and dehydrogenators 72 and 73 that respectively perform dehydrogenation of the linear hydrocarbon and the branched hydrocarbon that are separated in the separator 71.

In addition, the production apparatus 100 includes dehydrogenated product lines that respectively supply the first extractive distillation column 21 with a linear hydrocarbon dehydrogenated product obtained through dehydrogenation of the linear hydrocarbon in the dehydrogenator 72 and a branched hydrocarbon dehydrogenated product obtained through dehydrogenation of the branched hydrocarbon in the dehydrogenator 73.

The production apparatus 100 also includes a hydrogenator 80 that hydrogenates a residue that flows out from the bottom of the distillation column 51, a residue that flows out from the bottom of the distillation column 61, a residue that flows out from the top of the stripping column 42, and a residue that flows out from the top of the purification column 44, and hydrogen lines that supply the hydrogenator 80 with hydrogen produced in the dehydrogenators 72 and 73.

In the production apparatus 100, as a result of the first extractive distillation column 21 being supplied with the linear hydrocarbon dehydrogenated product and the branched hydrocarbon dehydrogenated product that are obtained through dehydrogenation of the linear hydrocarbon and the branched hydrocarbon in the dehydrogenators 72 and 73, it is possible to obtain isoprene and piperylene resulting from dehydrogenation of the linear hydrocarbon and the branched hydrocarbon, in addition to isoprene and piperylene that were contained in the hydrocarbon mixture, in the second distillation column 43 and the distillation column 61. Therefore, isoprene and piperylene can be efficiently obtained from the hydrocarbon mixture.

Moreover, through the production apparatus 100, dicyclopentadiene that is useful as a monomer or the like can be obtained in the distillation column 51.

Furthermore, through the production apparatus 100, a hydrogenated product that can be used as a gasoline base material or a feedstock for an ethylene cracker can be obtained in the hydrogenator 80. It is also possible to use hydrogen that is produced in dehydrogenation of the linear hydrocarbon and the branched hydrocarbon as hydrogen for production of this hydrogenated product. Therefore, the efficiency with which the hydrocarbon mixture serving as a feedstock is used can be further increased and various hydrocarbons can be produced in a highly efficient manner.

Although the presently disclosed hydrocarbon production apparatus is described above using one example, the presently disclosed hydrocarbon production apparatus is not limited to the example described above.

Specifically, the dimerizer 11 and the predistillation column 12 may be omitted from the presently disclosed production apparatus. Moreover, the separator 71 may be omitted from the presently disclosed production apparatus. Furthermore, the presently disclosed production apparatus may perform oxidative dehydrogenation of the linear hydrocarbon and the branched hydrocarbon or, alternatively, may perform dehydrogenation or oxidative dehydrogenation of just one of the linear hydrocarbon and the branched hydrocarbon. The hydrogenator 80 may also be omitted from the presently disclosed production apparatus. Moreover, the dehydrogenated product line may be a line that supplies the dehydrogenated product to the first distillation column 31 or the second extractive distillation column 41. Furthermore, the configurations of the isoprene purification section, the piperylene purification section, and the dicyclopentadiene purification section are not limited to the examples described above, and the isoprene purification section, the piperylene purification section, and the dicyclopentadiene purification section may be omitted from the presently disclosed production apparatus.

EXAMPLES

The following provides a more detailed description of the present disclosure using examples. However, the present disclosure is not limited to these examples.

Example 1

Isoprene, piperylene, and dicyclopentadiene were produced in the hydrocarbon production apparatus illustrated in FIG. 1 using a C5 fraction having a composition indicated in Table 1 as the hydrocarbon mixture. Specifically, isoprene, piperylene, and dicyclopentadiene were produced using a production apparatus 100 having the specifications shown below such that the produced amount of isoprene was 80,000 t/yr.

The used amount of the C5 fraction, the produced amounts of isoprene, piperylene, and dicyclopentadiene, the produced amount of hydrogen, the amount of a combusted fraction, the production amount of a hydrogenated product, and the effective use rate of a feedstock were determined. The results are shown in Table 2.

TABLE 1

| Component | Content [mass %] |
|---|---|
| C4 hydrocarbons | 1.7 |
| Isopentane | 16.5 |
| Pentene | 4.8 |
| Isoamylene | 6.0 |
| 2-Butyne | 0.4 |
| Isoprene | 13.0 |
| Pentane | 18.5 |
| 1,4-Pentadiene | 1.2 |
| Cyclopentadiene | 12.4 |
| Piperylene | 9.3 |
| Isohexane | 4.1 |
| Dicyclopentadiene | 6.2 |
| Others | 5.9 |

Figure 2:
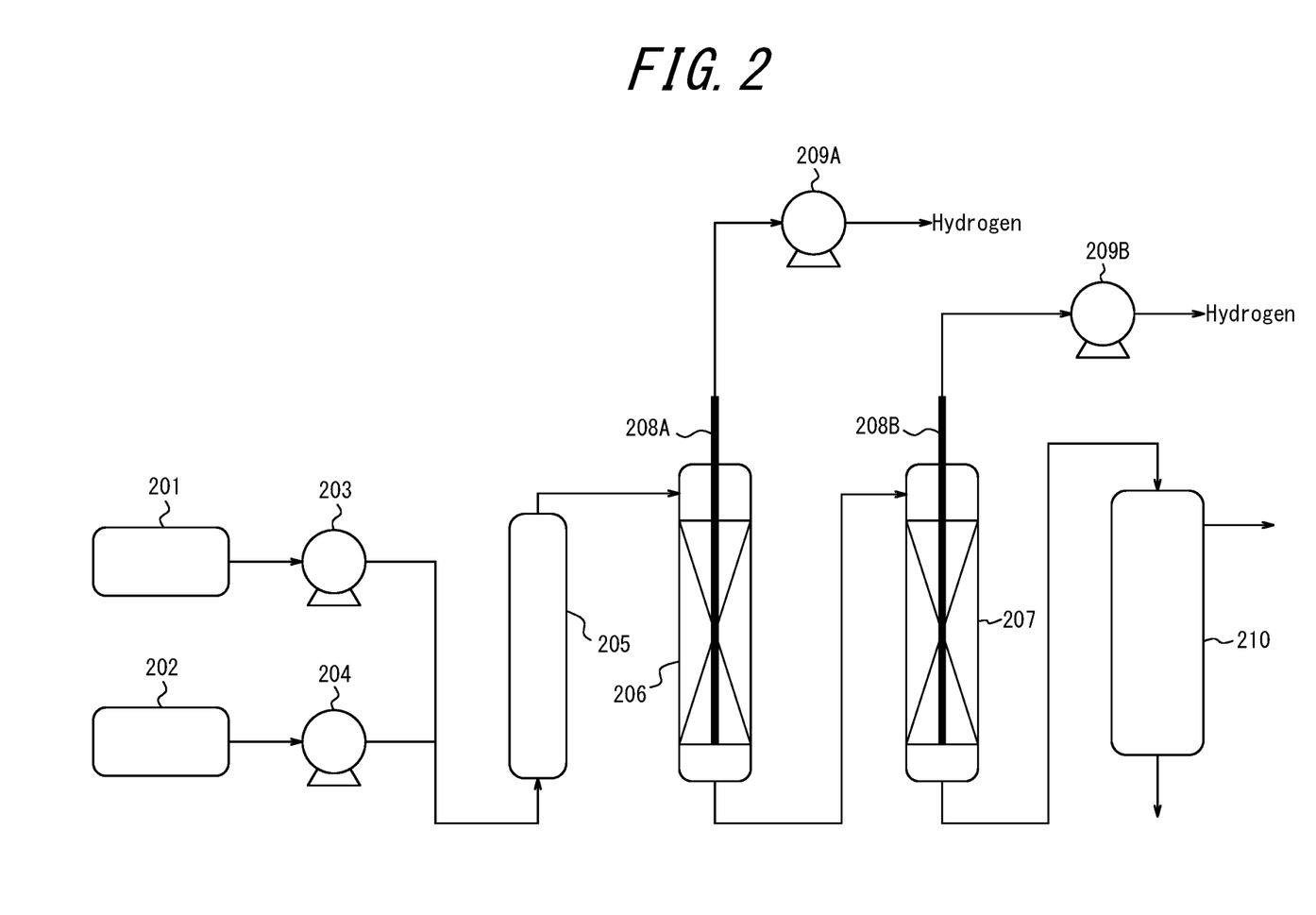
FIG. 2 is an explanatory diagram illustrating schematic configuration of a dehydrogenator that can be used in the hydrocarbon production apparatus illustrated in FIG. 1.

<Specifications>
[Separator 71]
A separator in which a silicalite membrane having mullite as a support was included as a separation membrane was used as the separator 71.
[Dehydrogenators 72 and 73]
A fixed bed distribution-type membrane reactor system configured as illustrated in FIG. 2 was used as the dehydrogenators 72 and 73. Note that in FIG. 2, 201 is the linear hydrocarbon or branched hydrocarbon, 202 is diluting water, 203 and 204 are pumps, 205 is a vaporizer, 206 is a dehydrogenation reactor (first stage; filled with K (1 mass %)-Pt (0.9 mass %)-Sn (0.3 mass %)/$ZrO_2$ catalyst prepared by impregnation method), 207 is a dehydrogenation reactor (second stage; filled with Pd (1 mass %)-Cu (4 mass %)-Mo (1 mass %)/$\gamma$-$Al_2O_3$ catalyst prepared by impregnation method), 208A and 208B are hydrogen separation membranes, 209A and 209B are vacuum pumps, and 210 is a condenser. A liquid dehydrogenated product flows out from a lower side of the condenser 210, whereas a gas dehydrogenated product flows out from an upper side of the condenser 210.

[Operating conditions of dehydrogenator 72]
  Temperature: 550° C.
  Linear hydrocarbon:water=1:11 Gas hourly space velocity (GHSV): 1,200 $hr^{-1}$
  Linear hydrocarbon conversion rate: 2.6 mol %
  Isoprene selectivity: 59.9 mol %
[Operating conditions of dehydrogenator 73]
  Temperature: 600° C.
  Branched hydrocarbon:water=1:11
  Gas hourly space velocity (GHSV): 1,200 $hr^{-1}$
  Branched hydrocarbon conversion rate: 19.4 mol %
  Isoprene selectivity: 77.8 mol %
[Hydrogenator 80]
A hydrogenator including a hydrogenation reactor (filled with Ni (60 mass %)/MgO—$SiO_2$ catalyst) after a thermal decomposition vessel was used as the hydrogenator 80.
[Operating conditions of hydrogenator 80]
  Thermal decomposition temperature: 350° C.
  Hydrogenation reaction temperature: 160° C.
  Gas hourly space velocity (GHSV): 370 $hr^{-1}$
  Supplied amount of hydrogen/amount of unsaturated bonds (equivalence ratio): 1.4

Comparative Example 1

Isoprene, piperylene, and dicyclopentadiene were produced in the same way as in Example 1 with the exception that the used production apparatus had the same configuration as the hydrocarbon production apparatus illustrated in FIG. 1 with the exception that the separator 71, the dehydrogenators 72 and 73, and the hydrogenator 80 were omitted and that combustion was carried out using the fraction (B) and residues as fuel.

Evaluations were conducted in the same manner as in Example 1. The results are shown in Table 2.

TABLE 2

|  | Example 1 | Comparative Example 1 |
|---|---|---|
| Used amount of C5 fraction [1000 t/yr] | 308.9 | 640.0 |
| Produced amount of isoprene [1000 t/yr] | 80.0 | 80.0 |
| Produced amount of piperylene [1000 t/yr] | 74.1 | 72.3 |
| Produced amount of dicyclopentadiene [1000 t/yr] | 42.6 | 88.3 |
| Produced amount of hydrogen [1000 $Nm^3$/yr] | 26560 | 0 |
| Produced amount of hydrogenated product [1000 t/yr] | 46.4 | 0 |
| Amount of combusted fraction [1000 t/yr] | 0 | 85.8 |
| Effective use rate of feedstock*[1] [mass %] | 64.5 | 37.6 |

*[1]Total produced amount of isoprene, piperylene, dicyclopentadiene, and hydrogen as proportion relative to used amount of C5 fraction It can be seen from Table 2 that in Example 1, the C5 fraction was effectively used and isoprene, piperylene, and the like were efficiently produced.

Note that in the hydrogenated product obtained in Example 1, unsaturated bonds of unsaturated hydrocarbons contained in the residues had all been hydrogenated. Upon evaluation using a spirosimulator, the ethylene yield was 29.3 mass % (reference naphtha: 30.7 mass %) and the propylene yield was 18.8 mass % (reference naphtha: 16.2 mass %), which is adequate for use as a feedstock in an ethylene cracker.

The compositions of the fraction (B) and residues that were combusted in Comparative Example 1 are respectively shown in Tables 3 and 4.

TABLE 3

| Component | Content [mass %] |
| --- | --- |
| C4 hydrocarbons | 0.2 |
| Isopentane | 35.1 |
| Pentene | 10.3 |
| Isoamylene | 12.4 |
| 2-Butyne | 0.0 |
| Isoprene | 0.5 |
| Pentane | 39.2 |
| 1,4-Pentadiene | 2.3 |
| Cyclopentadiene | 0.0 |
| Piperylene | 0.0 |
| Isohexane | 0.0 |
| Dicyclopentadiene | 0.0 |
| Others | 0.1 |

TABLE 4

| Component | Content [mass %] |
| --- | --- |
| C4 hydrocarbons | 0.0 |
| Isopentane | 0.0 |
| Pentene | 0.0 |
| Isoamylene | 0.0 |
| 2-Butyne | 1.1 |
| Isoprene | 2.0 |
| Pentane | 0.3 |
| 1,4-Pentadiene | 0.2 |
| Cyclopentadiene | 0.0 |
| Piperylene | 10.8 |
| Isohexane | 28.0 |
| Dicyclopentadiene | 34.8 |
| Others | 22.8 |

INDUSTRIAL APPLICABILITY

According to the present disclosure, it is possible to efficiently obtain isoprene and piperylene from a hydrocarbon mixture containing hydrocarbons having a carbon number of 5, such as a C5 fraction.

REFERENCE SIGNS LIST 11 dimerizer
12 predistillation column
21 first extractive distillation column
22 stripping column
31 first distillation column
41 second extractive distillation column
42 stripping column
43 second distillation column
44 purification column
51 distillation column
61 distillation column
71 separator
72, 73 dehydrogenator
80 hydrogenator
100 production apparatus

The invention claimed is:

1. A hydrocarbon production method for producing hydrocarbons, comprising:
a) pretreating a hydrocarbon mixture, where the pretreating comprises a step of dimerizing cyclopentadiene in the hydrocarbon mixture to obtain a hydrocarbon mixture containing dicyclopentadiene; and a step of using a predistillation column to perform distillation of the hydrocarbon mixture containing dicyclopentadiene to obtain
a pretreated hydrocarbon mixture and a fraction (E) enriched in dicyclopentadiene, wherein the pretreated hydrocarbon mixture further contains isoprene, piperylene, a linear $C_5$ hydrocarbon including one or fewer carbon-carbon double bonds, and a branched $C_5$ hydrocarbon including one or fewer carbon-carbon double bonds;
b) performing extractive distillation in a first extractive distillation column of the pretreated hydrocarbon mixture to produce a fraction (A) comprising an extractant enriched in isoprene and piperylene and a fraction (B) enriched in the linear hydrocarbon and the branched hydrocarbon having lower solubility than isoprene and piperylene in the extractant;
c) performing distillation of a fraction obtained after separation of the extractant from the fraction (A) to obtain a fraction (C) enriched in isoprene and a fraction (D) enriched in piperylene;
d) separating the linear and branched hydrocarbon contained in fraction (B);
e) a dehydrogenation step of performing dehydrogenation or oxidative dehydrogenation of at least one of the separated linear hydrocarbon and the separated branched hydrocarbon contained in the fraction (B) to obtain a dehydrogenated product including at least one of a linear hydrocarbon dehydrogenated product containing piperylene and a branched hydrocarbon dehydrogenated product containing isoprene;
f) determining a required production amount of isoprene and piperylene, wherein an amount of at least one of the linear and branched hydrocarbon is adjusted so that the isoprene and/or piperylene produced supplements a difference between the required amount of isoprene and piperylene and the amount of isoprene and piperylene produced from the extractive distillation;
g) a recovery step of supplying the dehydrogenated product to an extractive distillation column or a distillation column and obtaining at least one of isoprene and piperylene from the dehydrogenated product,
h) purifying the fraction (C) in an isoprene purification section including a second extractive distillation column to obtain high-purity isoprene;
i) purifying the fraction (D) in a piperylene purification section to obtain high-purity piperylene;
j) a dicyclopentadiene purification step of purifying the fraction (E) in a dicyclopentadiene purification section to obtain high-purity dicyclopentadiene; and
k) a hydrogenation step of hydrogenating at least one of a residue discharged in the isoprene purification step, a residue discharged in the piperylene purification step, and a residue discharged in the dicyclopentadiene purification step,
wherein at least one of the linear hydrocarbon and the branched hydrocarbon that is not dehydrogenated or oxidatively dehydrogenated in the dehydrogenation step is mixed with a hydrogenated product obtained in the hydrogenation step and used as a gasoline base material or a feedstock for an ethylene cracker.

2. The hydrocarbon production method according to claim 1, wherein the dehydrogenated product is supplied to the first extractive distillation column in the recovery step.

3. The hydrocarbon production method according to claim 1, wherein the hydrogenation is performed using hydrogen produced in the dehydrogenation step.

* * * * *